United States Patent
Jezior

(10) Patent No.: US 6,582,683 B2
(45) Date of Patent: *Jun. 24, 2003

(54) DERMAL BARRIER COMPOSITION

(75) Inventor: Bruce Jezior, Jupiter, FL (US)

(73) Assignee: Skinvisible Pharmaceuticals, Inc., Las Vegas, NV (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/477,745

(22) Filed: Jan. 4, 2000

(65) Prior Publication Data

US 2002/0051797 A1 May 2, 2002

(51) Int. Cl.[7] .......................... A61K 7/40; A61K 31/74; A01N 25/00; A01N 31/00; A01N 33/00; A01N 37/00; A01N 43/00; A01N 59/00; A01N 65/00

(52) U.S. Cl. ........................ 424/60; 424/59; 424/78.02; 424/78.03; 424/78.07; 424/613; 424/719; 424/750; 514/231.2; 514/241; 514/396; 514/399; 514/557; 514/617; 514/649; 514/671; 514/714; 514/721; 514/731; 514/772.3; 514/772.4; 514/772.5; 514/772.6; 514/772.7

(58) Field of Search .......................... 424/70.1, 70.11, 424/70.15, 59, 60, 78.02, 78.03, 78.07, 613, 719, 790; 514/771, 772.1, 772.2, 772.3, 231.2, 241, 396, 399, 557, 617, 649, 671, 714, 721, 731, 772.4, 772.5, 772.61, 772.7

(56) References Cited

U.S. PATENT DOCUMENTS

| | | | |
|---|---|---|---|
| 4,035,506 A | 7/1977 | Lucas et al. | |
| 4,301,145 A | 11/1981 | Cestari | |
| 4,448,906 A | 5/1984 | Deinet et al. | |
| 4,500,338 A | 2/1985 | Young et al. | |
| 4,507,279 A | 3/1985 | Okuyama et al. | |
| 4,645,794 A | 2/1987 | Davis et al. | 525/61 |
| 4,671,957 A | 6/1987 | Holtshousen | |
| 4,803,066 A | 2/1989 | Edwards | |
| 4,810,489 A | 3/1989 | Murray et al. | 424/59 |
| 4,897,259 A | 1/1990 | Murray et al. | 514/772.5 |
| 4,971,800 A | 11/1990 | Chess et al. | |
| 5,019,604 A | 5/1991 | Lemole | |
| 5,045,317 A | 9/1991 | Chess et al. | |
| 5,051,260 A | 9/1991 | Chess et al. | |
| 5,055,303 A | 10/1991 | Riley, Jr. | |
| 5,082,656 A | 1/1992 | Hui et al. | 514/24 |
| 5,126,136 A | 6/1992 | Merat et al. | |
| 5,155,199 A | 10/1992 | Hayashi | |
| 5,232,691 A | 8/1993 | Lemole | |
| 5,266,329 A | 11/1993 | Riley, Jr. | |
| 5,320,838 A | 6/1994 | Woller | 424/78.02 |
| 5,336,305 A | 8/1994 | Staats | 106/18.32 |
| 5,370,876 A | 12/1994 | Noll et al. | |
| 5,417,968 A | 5/1995 | Staats | 424/78.07 |
| 5,597,849 A | 1/1997 | McGinity et al. | 514/648 |
| 5,605,676 A | 2/1997 | Gaffar et al. | |
| 5,607,979 A | 3/1997 | McCreery | |
| 5,622,993 A | 4/1997 | McGinity et al. | 514/626 |
| 5,658,559 A | 8/1997 | Smith | 424/78.02 |
| 5,707,612 A | 1/1998 | Zofchak et al. | |
| 5,721,306 A | 2/1998 | Tsipursky et al. | 524/449 |
| 5,725,844 A | 3/1998 | Gers-Barlag et al. | 424/59 |
| 5,725,875 A | 3/1998 | Noll et al. | |
| 5,730,966 A | * 3/1998 | Torgerson et al. | 424/70.11 |
| 5,747,022 A | 5/1998 | Slavtcheff | 424/78.03 |
| 5,807,957 A | 9/1998 | Samour et al. | 528/49 |
| 5,834,538 A | * 11/1998 | deHullu et al. | 524/22 |
| 5,874,074 A | 2/1999 | Smith | 424/78.02 |
| 5,891,470 A | 4/1999 | Rinaldi et al. | |
| 5,906,822 A | 5/1999 | Samour et al. | |
| 5,911,980 A | 6/1999 | Samour et al. | |
| 5,939,453 A | 8/1999 | Heller et al. | |
| 5,942,545 A | 8/1999 | Samour et al. | |
| 5,955,109 A | 9/1999 | Won et al. | |
| 5,968,543 A | 10/1999 | Heller et al. | |
| 5,968,919 A | 10/1999 | Samour et al. | |
| 5,976,566 A | 11/1999 | Samour et al. | |
| 5,980,876 A | * 11/1999 | Peffly | 424/70.12 |
| 6,096,344 A | 8/2000 | Liu et al. | |

FOREIGN PATENT DOCUMENTS

| | | |
|---|---|---|
| EP | 640352 | 3/1995 |
| EP | 747062 | 12/1996 |
| EP | 391741 | 4/1998 |
| JP | 10095714 A * | 9/1996 |

OTHER PUBLICATIONS

Noguchi et al., "Hair treatment agent—includes specific high molecular copolymer compounds by which skin layer is made to form on hair surface," Derwent Abstract (ACC#1998–280363; Week#199825), 1999.*

(List continued on next page.)

Primary Examiner—S. Mark Clardy
Assistant Examiner—Frank Choi
(74) Attorney, Agent, or Firm—Merchant & Gould P.C.

(57) ABSTRACT

Disclosed is a dermal barrier composition which contains a hydrophilic polymer emulsion and a hydrophobic polymer emulsion. The dermal barrier composition is moisture activated, and remains inert until the hydrophobic and hydrophilic polymer emulsions contact a suitable substrate such as human skin. The dermal barrier composition is itself an emulsion, and can optionally contain a biocidal agent for antimicrobial and antiviral efficacy. The dermal barrier composition can also contain other active agents such as sunscreens, insect repellents and fungicides. The dermal barrier composition can be applied topically to skin, where it forms a protective or barrier layer against a number of pathogenic and chemical irritants.

18 Claims, 6 Drawing Sheets

OTHER PUBLICATIONS

Bradley, C. et al., "Noninvasive Transdermal Chemical Collection", *Skin Pharmacol*, vol. 3, pp. 218–226 (1990).

Hasirci V., "Synthesis and characterization of PVNO and PVNO–PVP hydrogels", *Biomaterials*, vol. 2, No. 1, pp. 3–8 (Jan. 1981).

Material Safety Data Sheet, Gantrez S–97 BF Solution, ISP Technologies Inc., 6 pages (Apr. 7, 1994).

Material Safety Data Sheet, Ganex V–216, ISP Technologies, Inc., 5 pages (Sep. 16, 1994).

Material Safety Data Sheet, Ganex V–220, ISP Technologies Inc., 6 pages (Oct. 7, 1998).

Nair, P. et al., "Studies on the effect of degree of hydrophilicity on tissue response of polyurethane interpenetrating polymer networks", *Biomaterials*, vol. 13, No. 8, pp. 537–542 (1992).

Tiller et al., "Designing surfaces that kill bacteria on contact", http://www/pnas.org/cgi/content/abstract/98/11/5981, PNAS Online, 2 pages (May 22, 2001).

* cited by examiner

DERMAL BARRIER COMPOSITION

FIELD OF THE INVENTION

The invention relates generally to a dermal barrier composition, a protective layer for skin, a method for manufacturing the dermal barrier composition, a method for protecting skin tissue, and a method of holding active ingredients in close proximity to skin.

BACKGROUND OF THE INVENTION

The need for a protective hand lotion that not only provides protection against deleterious chemicals but also acts as an active antimicrobial and antiviral barrier has long been known in industries such as health care and food handling. In the health care industry, such a hand lotion would reduce the incidence of nosocomial infection transmission; not only between patients, but also between patient and staff. In the food handling industry, there has been an increasing awareness of food borne pathogens, both among manufacturers and the general public.

Vinyl gloves are often used to provide a level of protection against chemical and pathogenic substances. This level of protection is often less than optimal. The gloves serve to increase perspiration rate, which provides a rich medium for growth and proliferation of surface pathogens. Further, new gloves typically have a defect incidence rate as high as 50 to 96 percent. The combination of these two factors means that pathogens are inoculated through defects in the gloves to contacted materials or patients at much higher levels than if no protection was used at all.

Work practices to date have identified frequent handwashing as the most effective tool at reducing pathogenic transfer or inoculation. Unfortunately, frequent handwashing leads to increased resistance by employees, as frequent exposure to water and detergents results in de-lipidation of the dermal structures with resultant chaffing and painful contact dermatitis. While studies have shown that the use of emollient creams and lotions reduce these effects, such creams and lotions can require frequent application because they are easily washed off.

In addition to protection against pathogenic invaders, there is also a need for protection against a wide range of chemicals. These can range from substances which are locally damaging to dermal structures, such as caustic materials, to substances which are known to be absorbed through the dermis. Such materials can result in metabolic as well as mutagenic damage. A wide range of industries exhibit a need for protection against such chemicals. These include, for example, hair salons, where employees are subjected to caustic materials and dyes. A number of different industries utilize various hydrocarbons in manufacturing processes. Food processing industries subject employees to various herbicides, insecticides and fertilizers.

Antimicrobial barrier compositions for use on human skin are described, for example, in U.S. Pat. Nos. 5,336,305 and 5,417,968 to Staats. Hui et al, U.S. Pat. No. 5,082,656; and Smith, U.S. Pat. Nos. 5,658,559 and 5,874,074 also describe compositions for topical application.

SUMMARY OF THE INVENTION

A dermal barrier composition for topical application is provided by the invention. The dermal barrier composition includes a hydrophilic polymer emulsion and a hydrophobic polymer emulsion.

The hydrophilic polymer emulsion includes poly (methyl vinyl ether/maleic acid), poly (vinyl pyrrolidone/1-eicosene), and poly (vinyl pyrrolidone/1-hexadecene). The poly (methyl vinyl ether/maleic acid) is present in the hydrophilic polymer emulsion in an amount greater than either the poly (vinyl pyrrolidone/1-eicosene) or poly (vinyl pyrrolidone/1-hexadecene). The hydrophobic polymer emulsion includes poly (vinyl pyrrolidone/1-hexadecene), poly (vinyl pyrrolidone/1-eicosene), and poly (methyl vinyl ether/maleic acid). The poly (vinyl pyrrolidone/1-hexadecene) is present in the hydrophobic polymer emulsion in an amount greater than either the poly (vinyl pyrrolidone/1-eicosene) or poly (methyl vinyl ether/maleic acid). The emulsion may be formed as a viscous fluid that may be applied by hand, or alternatively by a spray or aerosol. Active components, such as biocides, become physically distributed in voids throughout the applied composition and remain efficacious during the period of protection.

The invention is found in a dermal barrier composition having a hydrophilic polymer emulsion and a hydrophobic polymer emulsion as described above in a ratio of about 1 to 1.

The invention is also found in a dermal barrier composition having a hydrophobic polymer emulsion and a hydrophobic polymer emulsion as previously described in a ratio of about 2.5 to 1. Both such compositions form barriers which block contact by harsh or toxic materials from the skin for appreciable time periods in a workplace environment, without inhibiting natural excretion of fluids from the skin.

The invention is also found in a dermal barrier layer including a dermal barrier composition prepared by mixing a hydrophilic polymer emulsion and a hydrophobic polymer emulsion; wherein the dermal barrier emulsion, when applied to dry fritted glass in a thickness of about 0.5 to about 0.85 millimeters and allowed to bond to said glass for a period of 30 seconds, provides a film which remains at least about 80 percent adhered to the fritted glass after treatment with a 5% ammonium hydroxide for a period of 3 hours. When applied to the skin, the barrier strongly adheres to the stratum corneum and thereafter depletes only slowly.

Other aspects of the invention include methods of making dermal barrier compositions as previously described, which optionally can include encapsulated active agents such as biocides, fungicides, sun screens and insect repellents.

The invention is found in a method for protecting skin tissue against excessive moisture loss, said method including the steps of washing skin tissue to form cleansed skin tissue, and contacting said cleansed skin tissue with the dermal barrier emulsion described above.

The invention is found in a method of carrying and holding an active agent in proximity to skin tissue, the method including the steps of washing skin tissue to form cleansed skin tissue, and contacting the cleansed skin tissue with the dermal barrier emulsion described above.

Another feature in accordance with the invention is that the film forms a protective barrier that is comparable with the body's need to excrete liquids from the skin, while blocking access to higher molecular weight materials from the workplace environment. This results from the fact that the barrier is physically integral except for distributed micro-openings of irregular outline which permit this anistropic function to exist. Protective properties which last for hours in use, and which meet or exceed the properties of protective gloves are thus provided with greater convenience and comfort than gloves.

DETAILED DESCRIPTION

Figure 1:
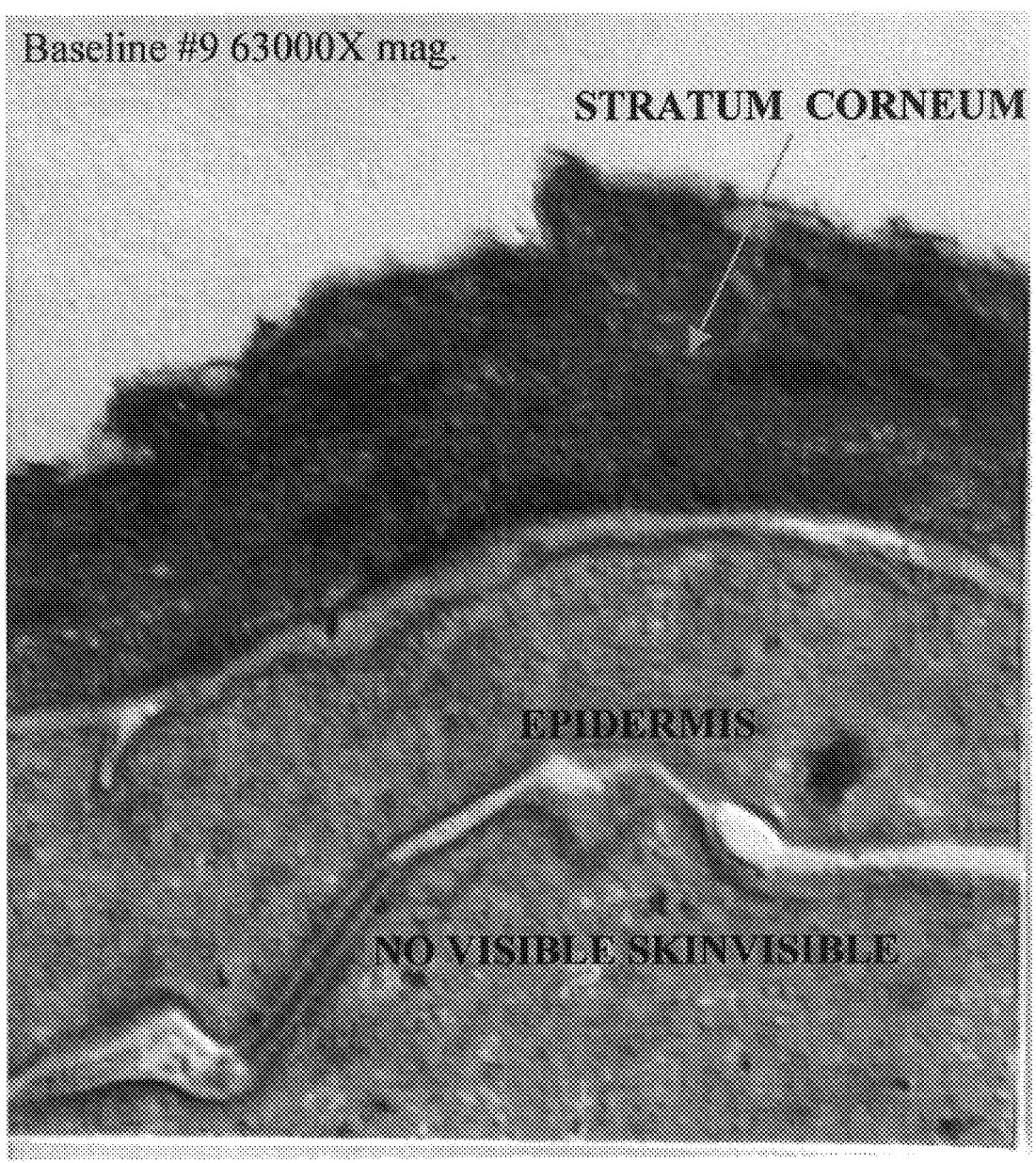
FIGS. 1 through 4 are transmission electron microscopy views showing the cross-sections of a dermal barrier composition of the present invention as existing on the human skin at different times over a four hour interval.

A dermal barrier composition for topical application is provided by the invention that is particularly suitable for health care, food service and other environments where harsh or toxic materials may be encountered. The composition is temperature, moisture and substrate activated. This means that when the composition encounters a suitable substratum such as skin at a temperature above ambient and under dehydrating conditions, the composition undergoes conformational changes. As a result of the conformational changes, helical fibers within the composition align with each other, creating "sticky ends" which result in a barrier matrix of high molecular weight. These fibers become nearly irreversibly bound to the substrate by very strong ionic, hydrophilic and hydrophobic forces.

The three dimensional nature of the substrate (the skin to which the composition can be applied) orders the alignment of the polymer fibers along the surface of the substrate. This alignment facilitates the interactions of "sticky ends" between adjacent polymer strands, raising their apparent molecular weights and creating an ordered and highly impermeable matrix having interstitial space suitable for holding desired active agents. This alignment is facilitated by the dehydrating conditions of the drying process. Alignment occurs in solution as well, albeit at a much slower rate. This continues for a period of 4 to 6 hours, until through natural turnover of the stratum corneum and depletion of the polymer substrate, the polymer layer is shed. Micro-openings or fenestrations in the matrix, however, to exist sufficient to allow escape of excreted matter from the skin.

An advantage of the dermal barrier composition is that it can be provided without alcohols or other solvents. Furthermore, the dermal barrier composition can be provided without typical skincare components such as oils and waxes.

The dermal barrier compositions of the invention include a hydrophilic polymer emulsion and a hydrophobic polymer emulsion. The hydrophobicity of each polymer emulsion is defined by the water-solubility of its continuous phase. The hydrophilic polymer emulsion contains a continuous phase which is soluble in water while the hydrophobic polymer emulsion has a water insoluble continuous phase. In this, water solubility is defined as greater than 80 percent solubility. By including a hydrophilic polymer emulsion and a hydrophobic polymer emulsion, an emulsion is provided which can provide a long lasting barrier layer. Typically, a useful life of in excess of 4 hours of normal activity is provided, at which time reapplication is readily effected.

The invention includes three polymers which are used in different proportions to separately create a hydrophilic polymer emulsion and a hydrophobic polymer emulsion. The hydrophilic polymer emulsion contains a large percentage of a hydrophilic polymer and smaller amounts of several hydrophobic polymers. Conversely, the hydrophobic polymer emulsion contains a large percentage of a hydrophobic polymer and smaller amounts of a hydrophilic polymer and a second hydrophobic polymer. Typically the ratios are about 3:1 or less.

Furthermore, the individual hydrophilic and hydrophobic components cooperate to encapsulate the desired active ingredient. When the hydrophilic and hydrophobic polymers are combined and allowed to cool, polymer strands coil together nearly irreversibly to form super-helices containing multiple polymer strands. Within these multiple strands are voids (or micro-environments) which can be hydrophilic, hydrophobic, or somewhere in between. These voids entrap or encapsulate active agents which can be either water soluble or water insoluble.

Hydrophilic Polymer Emulsion

As described in the present invention, the hydrophilic polymer emulsion includes a hydrophilic polymer and other polymers. In a preferred embodiment, the hydrophilic polymer emulsion includes poly (methyl vinyl ether/maleic acid), poly (vinyl pyrrolidone/1-eicosene) and poly (vinyl pyrrolidone/1-hexadecene).

In a preferred embodiment, the hydrophilic polymer emulsion includes about 85 to 92 wt-% poly (methyl vinyl ether/maleic acid), about 3 to 7 wt-% poly (vinyl pyrrolidone/1-eicosene), and about 4 to 8 wt-% poly (vinyl pyrrolidone/1-hexadecene).

One of the polymers used in the invention contains maleic acid. Maleic acid has a pH of about 2.5 and is negatively charged at neutral pH. It becomes a salt as it is neutralized. The hydrophilic polymer emulsion has a pH of between 1.5 and 2.5. The individual polymer components cooperate to form a charge-neutral mixture at neutral pH. In one embodiment, it has been found that the ratio of hydrophilic polymer emulsion to hydrophobic polymer emulsion is about 1 to 1.

In another embodiment, the ratio of hydrophilic polymer emulsion to hydrophobic polymer emulsion is about 2.5 to 1. While performing similarly to the formulation in which the polymer emulsions are in a 1 to 1 ratio, this embodiment has an aesthetic advantage in that it does not become tacky after application.

It has been found that permeability increases as the relative amount of the hydrophobic polymer emulsion decreases. This is undesirable, as an increase in permeability negatively impacts the barrier characteristics of the dermal barrier composition of the invention. However, a ratio of about 2.5 to 1 provides an effective barrier composition. This ratio can vary all the way from about 1 to 1 to about 2.5 to 1.

The polymer components of the dermal barrier composition are preferably sufficiently small so that they mix and sufficiently large that they provide barrier properties. It is believed that if the polymers are too small, they will not provide the desired barrier properties. In addition, if the polymers are too large, it is believed that they will not sufficiently mix. The poly (methyl vinyl ether/maleic acid) preferably has a number average molecular weight of less than about 95,000, more preferably about 70,000. The poly (vinyl pyrrolidone/1-eicosene) and poly (vinyl pyrrolidone/1-hexadecene) have number average molecular weights of at least about 5000. More preferably, they have number average molecular weights of about 8600 and 7300, respectively.

These polymers which can be used in the dermal barrier composition can be block or random copolymers. Each of these polymers are known barrier formers and are available from International Specialty Products. The poly (methyl vinyl ether/maleic acid) is available as Gantrey S97®, the poly (vinyl pyrrolidone/1-eicosene) is available as Ganex V220®, and the poly (vinyl pyrrolidone/1-hexadecene) is sold as Ganex V216®.

These particular polymers are selected partially because of a need to balance potential charges. More particularly, poly (methyl vinyl ether/maleic acid) is selected for its water solubility. The two hydrophobic polymers are selected because they both have the ability to form helical structures when heated Hydrophobic Polymer Emulsion As described in the present invention, the hydrophobic polymer emulsion includes a hydrophobic polymer and other polymers. In a preferred embodiment, the hydrophobic polymer emulsion includes poly (vinyl pyrrolidone/1-hexadecene), poly (vinyl pyrrolidone/1-eicosene), and poly (methyl vinyl ether/maleic acid).

In a preferred embodiment, the hydrophobic polymer emulsion includes about 87 to 95 wt-% poly (vinyl pyrrolidone/1-hexadecene), about 3 to 8 wt-% poly (vinyl pyrrolidone/1-eicosene), and about 2 to 6 wt-% poly (methyl vinyl ether/maleic acid). The number average molecular weights of these three polymers are as defined previously in regards to the hydrophilic polymer emulsion. When the hydrophilic polymer emulsion and the hydrophobic polymer emulsion are mixed at a ratio of 1:1, the resulting composition has a range of components, based upon the above embodiment of the hydrophilic polymer emulsion and the hydrophobic polymer emulsion, of 43.5 wt. % to 48 wt. % poly (methyl vinyl ether/maleic acid), 3 wt. % to 7.5 wt. % poly (vinyl pyrrolidone/1-eiocosene), and 45.5 wt. % to 51.5 wt. % poly (vinyl pyrrolidone/1-hexadecene). When the hydrophilic polymer emulsion and the hydrophobic polymer emulsion are mixed at a ratio of 2.5:1, the resulting composition contains 61.3 wt. % to 69.6 wt. % poly (methyl vinyl ether/maleic acid), 3 wt. % to 7 wt. % poly (vinyl pyrrolidone/1-eiocosene), and 27.7 wt. % to 32.9 wt. % poly (vinyl pyrrolidone/1-hexadecene).

Active Agents

The formulations of the present invention can include a number of possible active agents. Examples include biocides, fungicides, insecticides and sunscreens. A number of biocidal agents are known to those of skill in the art, including quaternary ammonium compounds and peroxygen compounds such as peroxy acids. In a preferred embodiment, the dermal barrier compositions of the invention include a biocidal agent sold under the tradename Triclosan®. Preferably, this agent is present at a concentration of about 0.9 to about 1.1 wt-%, more preferably about 1.0 wt-%. Triclosan® gives a broad spectrum of pathogenic coverage and has a long history of safe usage with a benign toxicological profile. Triclosan® is a chlorinated diphenyl ether having the chemical structure shown below:

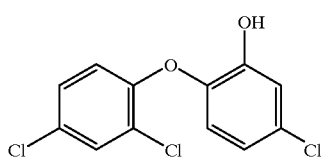

In another embodiment, the dermal barrier compositions contemplated by the present invention can successfully carry a variety of fungicidal agents, including sulconazole and naftifine. Additionally, antifungal agents such as morpholines, allylamines and triazoles can also be used.

Preferred fungicides include clotrimazole and miconazole nitrate, the structures of which are shown below, respectively:

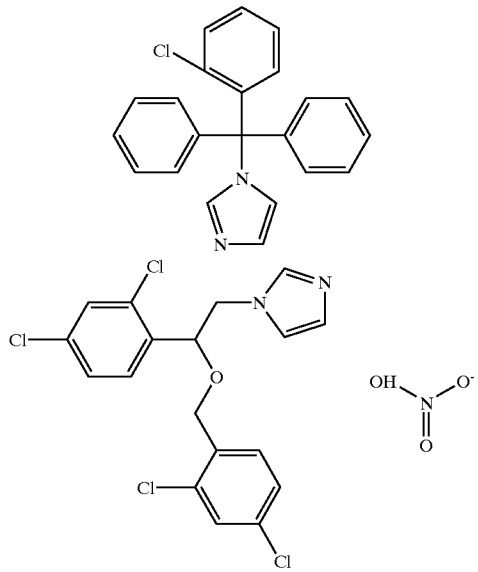

The dermal barrier compositions of the present invention can also be used as long lasting carriers for insecticides. A number of insecticides are known in the art as safe for human use, including citronella. Preferred insecticides include N,N'-diethyl-3-methylbenzamide, commonly known as DEET.

This insecticide has the structure shown below:

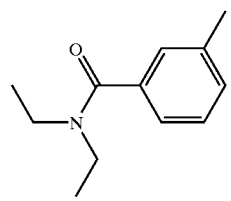

Another preferred use of the dermal barrier compositions of the present invention is as a long lasting carrier sunscreen. A number of FSDA approved materials are known, such as Aminobenzoic Acid-PABA, Cinoxate, Diethanolamine methoxycinnamate, Digalloyl trioleate, Dioxybenzone, Ethyl 4[bis(hydroxypropyl)]aminobenzoate, Glyceryl aminobenzoate, Homosalate, Lawsone with dihydroxyacetone, Mentyl anthranilate, Octocrylene, Octyl methoxycinnamate, Octyl Salicylate, Oxybenzone:Benzophenone, Padimate, Phenylbenzimidazole sulfonic acid, Red Petrolaum, Sulisobenzone, Titanium dioxide, Trolamine salicylate, and combinations of the above. Preferred sun screen materials include a mixture of octyl methoxycinnamate and benzophenone, which are shown below, respectively:

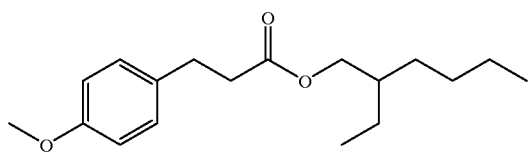

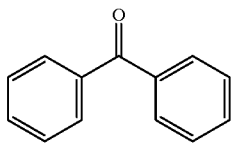

It has been found that the dermal barrier compositions of the present invention can accommodate a large variety of active agents. They can be water soluble or insoluble. If the active agent is highly volatile, it can not be added to the formulation until the temperature of the formulation has dropped sufficiently.

The dermal barrier compositions of the present invention have been found useful in encapsulating a wide range of potential actives.

Desirable actives include the following:

| Active Component | Purpose |
|---|---|
| Benzalkonium Chloride | antimicrobial |
| Benzophenone | sun screen |
| Glycerin | skin moisturizer |
| Iodine | antimicrobial |
| Vitamin A | skin healing |
| Vitamin D & D2 | skin healing |
| Aloe | skin healing |
| Octyl methoxycinnamate | sun screen |
| Anise Oil | Bass fishing lure |
| Garlic Oil | Bass fishing lure |
| Hydrocortisone | anti-inflammatory |
| Salicylic Acid | acne preparation |
| DEET | Insect Repellent |
| Phenol-TEA complex | antimicrobial |
| clotrimazole | antifungal |
| Miconazole Nitrate | antifungal |

The dermal barrier compositions of the invention can utilize a number of other ingredients in addition to the polymers and active agent. Examples of possible components includes aloe and glycerine, which are used for their lotion characteristics and as moisturizers. These components improve the spreadability and feel of the compositions of the invention. The barrier compositions can include preservatives such as Germall plus® and thickening agents such as Carbopol 940® or Carbopol Ultrez-10®. Germall plus® is a substituted urea, while the Carbopol materials are believed to be carboxypolymethylenes, which are vinyl polymers having active carboxyl groups. Carbopol 940® and Carbopol Ultrez-10® are available from B. F. Goodrich, and Germal +® is available from ISP.

Triclosan® is not water soluble. Consequently, the dermal barrier compositions of the invention can also include solvents for the Triclosan®. Examples of suitable solvents include Nonoxynol 9® and triethanolamine.

Exemplary formulations of the present invention include the following:

| Biocidal Formulation 1 | |
|---|---|
| Component | Weight Percent |
| hydrophilic emulsion | 4.0 |
| hydrophobic emulsion | 4.0 |
| water | 76.5 |
| Triclosan ® | 1.0 |
| glycerine | 5.0 |
| Nonoxynol 9 ® | 5.0 |
| aloe | 3.0 |
| Carbopol 940 ® | 0.5 |
| Germall plus ® | 0.5 |
| triethanolamine | 0.5 |

| Biocidal Formulation 2 | |
|---|---|
| Component | Weight Percent |
| hydrophilic emulsion | 4.00 |
| hydrophobic emulsion | 4.00 |
| water | 76.00 |
| Triclosan ® | 1.00 |
| glycerine | 5.00 |
| Nonoxynol 9 ® | 5.00 |
| aloe (10% solution) | 3.00 |
| Carbopol Ultrez-10 ® | 0.45 |
| Germall plus ® | 0.50 |
| triethanolamine | 1.05 |

| Biocidal Formulation 3 (Aerosol) | |
|---|---|
| Component | Weight Percent |
| Water | 78.9% |
| Polyethylene glycol | 2.0% |
| Glycerin | 5.0% |
| Nonoxynol-9 | 1.0% |
| Triclosan | 1.0% |
| Aloe | 3.0% |
| Hydrophilic emulsion | 4.0% |
| Hydrophobic emulsion | 4.0% |
| Triethanolamine | 0.6% |
| Germall Plus ® | 0.5% |

| Antifungal Formulation 1 | |
|---|---|
| Component | Weight Percent |
| hydrophilic emulsion | 5.00 |
| hydrophobic emulsion | 2.00 |
| water | 77.00 |
| glycerin | 5.00 |
| Nonoxynol-9 ® | 5.00 |
| aloe (10% solution) | 3.00 |
| Carbopol Ultrez-10 ® | 0.45 |
| Germall Plus ® | 0.50 |
| triethanolamine | 1.05 |
| Chlortrimazole | 1.00 |

| Antifungal Formulation 2 | |
| --- | --- |
| Component | Weight Percent |
| hydrophilic emulsion | 5.00 |
| hydrophobic emulsion | 2.00 |
| water | 77.00 |
| glycerin | 5.00 |
| Nonoxynol-9 ® | 5.00 |
| aloe (10% solution) | 3.00 |
| Carbopol Ultrez-10 ® | 0.45 |
| Germall Plus ® | 0.50 |
| triethanolamine | 1.05 |
| miconazole nitrate | 1.00 |

| Acne Formulation | |
| --- | --- |
| Component | Weight Percent |
| hydrophilic emulsion | 4.00 |
| hydrophobic emulsion | 4.00 |
| water | 74.00 |
| glycerin | 5.00 |
| Nonoxynol-9 ® | 5.00 |
| aloe (10% solution) | 3.00 |
| Carbopol Ultrez-10 ® | 0.45 |
| Germall Plus ® | 0.50 |
| triethanolamine | 1.05 |
| Triclosan | 1.00 |
| salicylic acid | 2.00 |

| Sunscreen Formulation | |
| --- | --- |
| Component | Weight Percent |
| hydrophilic emulsion | 5.00 |
| hydrophobic emulsion | 2.00 |
| water | 73.00 |
| glycerin | 5.00 |
| Nonoxynol-9 ® | 5.00 |
| aloe (10% solution) | 3.00 |
| Carbopol Ultrez-10 ® | 0.45 |
| Germall Plus ® | 0.50 |
| triethanolamine | 1.05 |
| octyl methoxycinnamate | 3.00 |
| benzophenone* | 2.00 |

*Can be omitted if high enough SPF factor can be obtained without it.

| Skin Moisturizer and Healing Formulation | |
| --- | --- |
| Component | Weight Percent |
| hydrophilic emulsion | 5.00 |
| hydrophobic emulsion | 2.00 |
| water | 78.00 |
| glycerin | 5.00 |
| Nonoxynol-9 ® | 5.00 |
| aloe (10% solution) | 3.00 |
| Carbopol Ultrez-10 ® | 0.45 |
| Germall Plus ® | 0.50 |
| triethanolamine | 1.05 |

| Insect Repellent Formulation 1 | |
| --- | --- |
| Component | Weight Percent |
| hydrophilic emulsion | 5.00 |
| hydrophobic emulsion | 2.00 |
| water | 76.00 |
| glycerin | 5.00 |
| Nonoxynol-9 ® | 5.00 |
| aloe (10% solution) | 3.00 |
| Carbopol Ultrez-10 ® | 0.45 |
| Germall Plus ® | 0.50 |
| triethanolamine | 1.05 |
| citronella oil | 2.00 |

| Insect Repellent Formulation 2 | |
| --- | --- |
| Component | Weight Percent |
| hydrophilic emulsion | 5.00 |
| hydrophobic emulsion | 2.00 |
| water | 48.00 |
| glycerin | 5.00 |
| Nonoxynol-9 ® | 5.00 |
| aloe (10% solution) | 3.00 |
| Carbopol Ultrez-10 ® | 0.45 |
| Germall Plus ® | 0.50 |
| triethanolamine | 1.05 |
| DEET | 30.00 |

Biocides

There are a number of food borne pathogens which together cause nearly 100 million cases of food poisoning in the United States each year. Food pathogens are tiny living organisms that grow in improperly handled food. The four primary food pathogens are *Staphylococcus aureus, Salmonella typhi, Clostridium perfringens* and *Clostridium botulinum.*

Pathogenic bacteria also include *Listeria monocytogenes, Streptococcus pyogenes, Shigella dysentariae, Vibrio vulnificus, Bacillus cereus,* and the so-called super bugs, such as *Enterococcus faecalis.* While each bacterial infection has its characteristic symptoms, they typically include fever, nausea, joint pain and various gastrointestinal discomforts.

Viruses differ from bacteria in that they are not an independently living organism—they are not capable of replicating without a host. Although they are too small to replicate without entering a living cell (500,000,000 common cold viruses can fit on the head of a pin), they do contain fundamental genetic information (DNA or RNA).

When a virus enters a living cell a viral infection has occurred. The virus needs this living cell to multiply. As the cell's machinery and enzymes aid the virus in its replication, the new virus then leaves the cell to infect additional cells. Viruses can leave a cell one at a time by a process known as budding, or they can leave by lysis, a process in which the host cell erupts and all virus copies are released at once. One million copies of a Poliomyelitis virus can be found in only one cell in an infected human intestine.

Viruses can mutate (change genetic identity). In some instances, mutation leads to the inability of the virus to infect a cell. In other cases however, the virus may mutate into a new infective strain. This insures survival of the viral species and represents a new lineage of infection for the human host. The influenza virus regularly presents new strains by mutation, thus creating the need for a "new vintage" of flu vaccine every year.

Our bodies have specific methods for combating the spread of viral infections. One is through the synthesis and secretion of interferons, proteins that interact with the cells adjacent to the infected cell(s), making them more resistant to viral infection. If interferon is not enough to stop the spread of the infection, our body's immune system begins to develop the mechanisms to kill the virus and the cells infected by it.

HIV infects the human immune system cells and thereby creates a special problem. By damaging the body's response system to infection, the virus continues replicating unimpeded resulting in the death of these immune cells representing the host's defense leading toe the AIDS disease and unfortunately death of the host.

Viruses are notoriously difficult to kill even for industrial rated surface disinfectants. It is not difficult to see why institutional outbreaks of infection can become endemic when infectious virus particles can survive for days on experimentally contaminated non-porous inanimate surfaces and on human hands for several hours. Infectious particles can be recovered from hands of nurses caring for gastroenteritis infected patients as well as day care workers in child care facilities where infected children are resident.

Studies examining virus survival following wash protocols utilizing hospital grade antimicrobial soaps fare even worse than surface disinfectants with some antimicrobial soaps producing little more effect on viruses than tap water washes. This has led many investigators to conclude that hand washing with antimicrobial scrubs may produce its greatest effect due to the physical effect of viral particle "wash-off" rather than any virocidal effect of the antimicrobial soap agent used. The ability of a barrier lotion that resists adherence of particulate matter may therefore play an even greater role in preventing transmission of infectious particles.

When looking at the resistance of viruses to killing agents, there appears to be an important feature in virus structure that indicates its susceptibility to being killed. This structure is the envelope surrounding the virus particle. Although one might think that the envelope surrounding the viral particle might impart added protection, these envelope viruses are the most susceptible to death when placed in contact with a chemical agent with known antiviral properties. Some NON-envelope viruses are known to be resistant to even the effects of 70% alcohol.

Nonoxynol-9® is one such agent that when placed in contact with envelope viruses will produce this deleterious effect. Some of these envelope viruses that are known human pathogens include the Influenza Virus, Herpes Simplex Virus, Respiratory Syncytial Virus (RSV), Vaccinia Virus and of course the virus causing AIDS, Human Immunodeficiency Virus (HIV).

Occupational Hand Dermatitis

Occupational hand dermatitis (OHD) is a loss of skin integrity characterized by inflammation, dryness, itching, lesions and erythema, or superficial redness. The two major medical indicators of OHD are skin moisture content and trans-epidermal water loss (TEWL), as a particular level of water content is necessary in helping the stratum corneum remain flexible, elastic and impermeable to bacteria, viruses and chemicals. An unusually low skin moisture content or unusually high level of TEWL water loss often indicates the presence of OHD.

OHD is most commonly caused via contact with water, detergent and dirt. The most injurious practice known is frequent handwashing. As a result, the occupations most at risk of OHD include hairdressers, food handlers and medical personnel. Additional causes of OHD include allergic reactions to latex gloves and irritants trapped under jewelry.

In addition to the dryness, etc., which characterize OHD, it is important to remember that OHD signifies a loss of skin integrity. As a result, moisture loss is accelerated, and the skin no longer forms an effective barrier against pathogenic and chemical intruders.

Chemical

The dermal barrier compositions of the present invention function as effective barriers against a number of common chemicals. Examples include acetone, which is the primary component in fingernail polish remover. Acetone can dehydrate the skin and can strip the skin of its natural oils. Formaldehyde is a common preservative also present in drywall and carpeting.

Ammonia is a common alkaline cleaner, as is sodium hypochlorite (bleach). Hydrogen peroxide is a hair colorant and a an antiseptic. Hydrochloric acid (muriatic acid) is commonly used as a tile and concrete cleaner. Sodium hydroxide is highly alkaline and is used in many cleaners. Baygon®, Malathion®, Dursban®/Chlorpyrifos®, Diazinon® and Atrazine® are all common pesticides. Perchloroethylene is a commonly used dry cleaning solvent which is a known liver carcinogen. A number of D&C dyes are known mutagens.

Antifungal

There are a number of skin fungi which cause a variety of skin problems. Symptoms of these fungal diseases include but are not limited to itching and/or burning, redness, flaking skin, blistering or rashes, and weeping lesions. Two of the most common skin fungi are *Trichophyton mentagrophyt* and *Trichophyton rubrum* which cause Athlete's foot and Jock Itch, respectively. The antifungal preparations described herein, may be used to cure or prevent these skin infections.

In all cases, the affected area should be washed with soap and water and thoroughly toweled dry. Antifungal preparations should be applied sparingly (sufficient to coat) and allowed to dry for a few minutes.

Insect Repellent

There are a variety of insect pests which consider humans a food source. Among these are fleas, ticks, mosquitoes, sand fleas, and no-see-ums (a biting midge). Many of these insects also carry diseases such as Rocky Mountain Spotted Fever, bubonic plague, malaria, yellow fever, Saint Louis encephalitis and as most recently appeared in the US, Dengue Fever.

As many of these insect-borne diseases carry a high mortality for humans, the best cure is prevention. Insect repellents prevent the bite of the carrier insect and hence the disease. The most effective chemical insect repellent is DEET (N,N'-diethyl-3-methylbenzamide), and an effective natural repellent is citronella oil. In both cases, the active ingredients are volatile, and readily lost from the skin surface within minutes to a couple of hours after application. This necessitates frequent reapplication. The dermal barrier preparation described herein extends the effectiveness of volatile active ingredients to 4–6 hours without the use of skin harming alcohols, waxes, oils, petroleum distillates or silicones.

In all cases, the affected area should be washed with soap and water and thoroughly toweled dry. Insect repellent preparations should be applied sparingly (sufficient to coat) and allowed to dry for a few minutes before sweating.

Sun Screen

Skin cancer is a growing concern among dermatologists, as skin cancer has become one of the fastest growing cancers. Indeed, tanning is the skin's response to protect itself from the harmful sun's rays by producing melanin granules. Skin cancer is avoidable by staying out of the sun or using sun screens when sun exposure is unavoidable.

As all known sun screens are water insoluble, the pharmaceutical industry has employed the use of alcohols, waxes, petroleum distillates, oils and silicones to dissolve sun screens and keep them on the skin. However, these ingredients are occlusive to the skin and generally are removed when swimming and sweating, and they do not promote healthy skin chemistry. All sun screens, regardless of how long they say they are effective, require reapplication after swimming, sweating or drying off with a towel.

The dermal barrier described herein when coupled with an effective sun screen agent such as Octyl methoxycinnamate bonds to the skin producing a long term barrier to UV that is not occlusive to the skin and lasts for 4–6 hours regardless of swimming, sweating, washing or toweling dry.

In all cases, the skin should washed with soap and water and thoroughly toweled dry. The sun screen preparation should be applied sparingly (sufficient to coat) and allowed to thoroughly dry for a few minutes prior to swimming or sweating.

Dermal barrier compositions can be prepared as described in Example 1. A preferred use for these compositions is described here. Basic use and application of the dermal barrier composition is the same, regardless of which active agent is included. Preferably, a user will thoroughly wash and dry their hands prior to application of the dermal barrier composition of the invention. For optimal protection, an antimicrobial soap should be used, with vigorous scrubbing for a period of one minute. After thorough drying, the user can apply approximately one milliliter of the dermal barrier composition to their hands. Preferably, the user will work the dermal barrier composition evenly into both sides of their hands. For continuous protection, it is preferred that the user apply the dermal barrier composition to their hands every four hours.

In most of the examples given above the composition is supplied as an emulsified lotion from a container and may readily be poured or squeezed out by a pump action. This is sanitary and convenient, but many prefer to use an aerosol or spray on formulation, because a spray can be even faster and require less effort. For example the formulation may be supplied at a spray station under a foot control, or by a co-worker. The "Biocidal Formulation 3" given above meets this goal, by inclusion of a small percentage of polyethylene glycol, which is a low molecular weight (6000–9000) polymer which binds water into the formulation. Consequently the emulsion is of lower viscosity but when ejected from a small nozzle under pressure forms into like small droplets which are uniform in properties.

The invention will now be described in more detail by reference to the following examples. The only proper construction of these examples is as non-limiting illustrative examples showing various formulations, stabilities, and applications of the invention.

EXAMPLES

Example 1

This example describes the preparation of a dermal barrier composition containing a biocidal agent. A biocidal agent is defined as a substance which has antimicrobial efficacy, antiviral efficacy, or a combination thereof. The hydrophilic and hydrophobic polymer emulsions are prepared independently prior to combination. Each polymer emulsion has the formulation given in Tables 1 and 2. The amount of each polymer is given as a weight percent of the hydrophilic or hydrophobic polymer emulsion.

TABLE 1 hydrophobic polymer emulsion

| Polymer | Content |
|---|---|
| poly (vinyl pyrrolidone/1-hexadecene) | 91 wt-% |
| poly (vinyl pyrrolidone/1-eicosene) | 6 wt-% |
| poly (methyl vinyl ether/maleic acid) | 3 wt-% |

The hydrophobic polymer emulsion is prepared by heating the poly (vinyl pyrrolidone/1-hexadecene) to 50 to 55° C. with constant agitation. The poly (methyl vinyl ether/maleic acid) is heated separately to 40 to 45° C. and is added to the poly (vinyl pyrrolidone/1-hexadecene). The mixture is heated to 60 to 65° C. The poly (vinyl pyrrolidone/1-eicosene) is heated to 40 to 45° C. and is slowly added to the mixture. The heat is removed and the mixture is allowed to cool to 40 to 45° C. with minimum agitation. If these temperatures are broadly exceeded, the polymers can be degraded.

TABLE 2 hydrophilic polymer emulsion

| Polymer | Content |
|---|---|
| poly (methyl vinyl ether/maleic acid) | 89 wt-% |
| poly (vinyl pyrrolidone/1-eicosene) | 5 wt-% |
| poly (vinyl pyrrolidone/1-hexadecene) | 6 wt-% |

The hydrophilic polymer emulsion is prepared by heating the poly (methyl vinyl ether/maleic acid) to 50 to 55° C. with constant agitation. The poly (vinyl pyrrolidone/1-hexadecene) is added to the poly (methyl vinyl ether/maleic acid) and is heated to 60 to 65° C. The poly (vinyl pyrrolidone/1-eicosene) is heated to 40 to 45° C. and added to the batch. The heat is removed and the mixture is allowed to cool with minimum agitation.

The dermal barrier composition is formed by combining the hydrophilic and hydrophobic polymer emulsions with other components, which are listed below:

| Component | Weight Percent |
|---|---|
| hydrophilic emulsion | 4.0 |
| hydrophobic emulsion | 4.0 |
| water | 76.5 |
| Triclosan ® | 1.0 |
| glycerine | 5.0 |
| Nonoxynol 9 ® | 5.0 |
| aloe | 3.0 |
| Carbopol 940 ® | 0.5 |
| Germall plus ® | 0.5 |
| triethanolamine | 0.5 |

Formulation of the dermal barrier composition continues with forming phase B, which is a mixture of triethanolamine, Nonoxynol-9® and Triclosan®. Next, phase A is formed by combining the hydrophilic polymer emulsion, the hydrophobic polymer emulsion, glycerine, aloe, Carbopol 940® and water. The mixture is combined and heated to 80° C. for at least 15 minutes. Then, phase B is combined with phase A. The mixture is allowed to cool to 50° C., at which a phase C, which includes the Germall plus®, is added.

The resulting composition preferably has a viscosity of between about 2,000 and about 3,000 centipoise. If the viscosity is too low, the composition is too thin to form an effective dermal barrier. Conversely, if the viscosity is too high, the composition is too thick or sticky to be effective or desired.

Example 2

This example demonstrates adhesion of the biocidal dermal barrier composition described in Example 1. A 5% solution of ammonium hydroxide was used to represent a typical harsh scrubbing or cleaner composition. In initial tests, dry fritted glass was used as a substrate. Fritted glass is a porous form of glass which is generally recognized in the dermatological industry as a passable model for human skin.

One drop (about 0.03 g) of the biocidal dermal barrier composition of Example 1 is carefully spread onto a 7.5 cm$^2$ fritted glass filter using a rubber "policeman". The actual amount is determined by weighing the entire fritted glass before and after application. Alternatively, the amount can be determined by weighing the loaded policeman before and after application to the surface.

Approximately 60 ml of 5% ammonium hydroxide (equivalent to household ammonia) is placed in one side of the chamber and allowed to absorb any lotion components after 3 and 6 hours.

After 3 and 6 hours, respectively, 20 ml aliquots of the solution are withdrawn and total solids (primarily polymers) are determined by evaporating the aliquot at 103° C. in a tared beaker. Weights of desorbed solids are divided by the surface area (7.5 cm$^2$) to determine mg/cm$^2$ levels. To determine weight percent of barrier composition desorbed, divide the milligrams of solids by the initial weight.

It was discovered that in an agitated bath, the biocidal dermal barrier layer bound firmly to the fritted glass. Only 18% of the biocidal dermal barrier layer released into the 5% ammonium hydroxide bath after 3 hours, while fully 68% of the biocidal dermal barrier layer remained on the glass after 6 hours.

In subsequent testing, the biocidal dermal barrier layer was applied to the forearm skin of human subjects. Using gauze soaked with 5% ammonium hydroxide, the treated forearm skin was scrubbed at intervals of 10 minutes, 2 hours and 4 hours. During testing, punch biopsies were taken for examination under both electron microscopy and atomic force microscopy. Under both examinations, the polymer was clearly seen with excellent adhesion to the underlying stratum corneum. As contact time increased between the polymeric lotion and the skin, the polymer appeared more evenly distributed.

Thirty four subjects, following a three day washout period with glycerin soap, had a baseline supervised 2 minute skin rubbing on the volar forearm with a gauze pad. The test article (0.1 m/0.04 gm) was then applied to the volar forearm and allowed to dry. Controlled rubbings with gauze pads were performed at approximately 10 minutes, two and four hours post application. Three millimeter biopsies were performed at baseline, 10 minutes, two and four hours post application of the test article on three subjects and submitted for electron and atomic force microscopy. In addition, baseline, 10 minutes, two and four hour gravimetric analysis was conducted.

A comparison of the gravimetric analysis' baseline weights with the 10 minutes, two and four hour treatments did not demonstrate any significant differences.

Tests conducted on different subjects as to the substantivity of the films at various times after application were carefully and minutely analyzed by extremely high resolution techniques. Samples were taken at the different intervals by 3 mm "punch biopsies" of the skins of some of the subjects, and half were then viewed in section by electron microscopy at 63,000× magnification, showing the baseline (untreated) condition (FIG. 1) the condition at 10 minutes after application (FIG. 2), the condition at 2 hours after application (FIG. 3) and then at four hours after application (FIG. 4).

The electron microscopy conducted on three subjects showed a distinct electron dense film substance at the upper most region of the stratum corneum. The dermal barrier is most pronounced at the two hour time frame, but can be distinguished at the 10 minute and four hour time frame. There was no identifiable film on the baseline specimens, as seen in FIG. 1. Thus, electron microscopy revealed a distinct electron dense dermal barrier band at 10 minutes, 2 hours and 4 hours (see FIGS. 2, 3 and 4).

Figure 2:
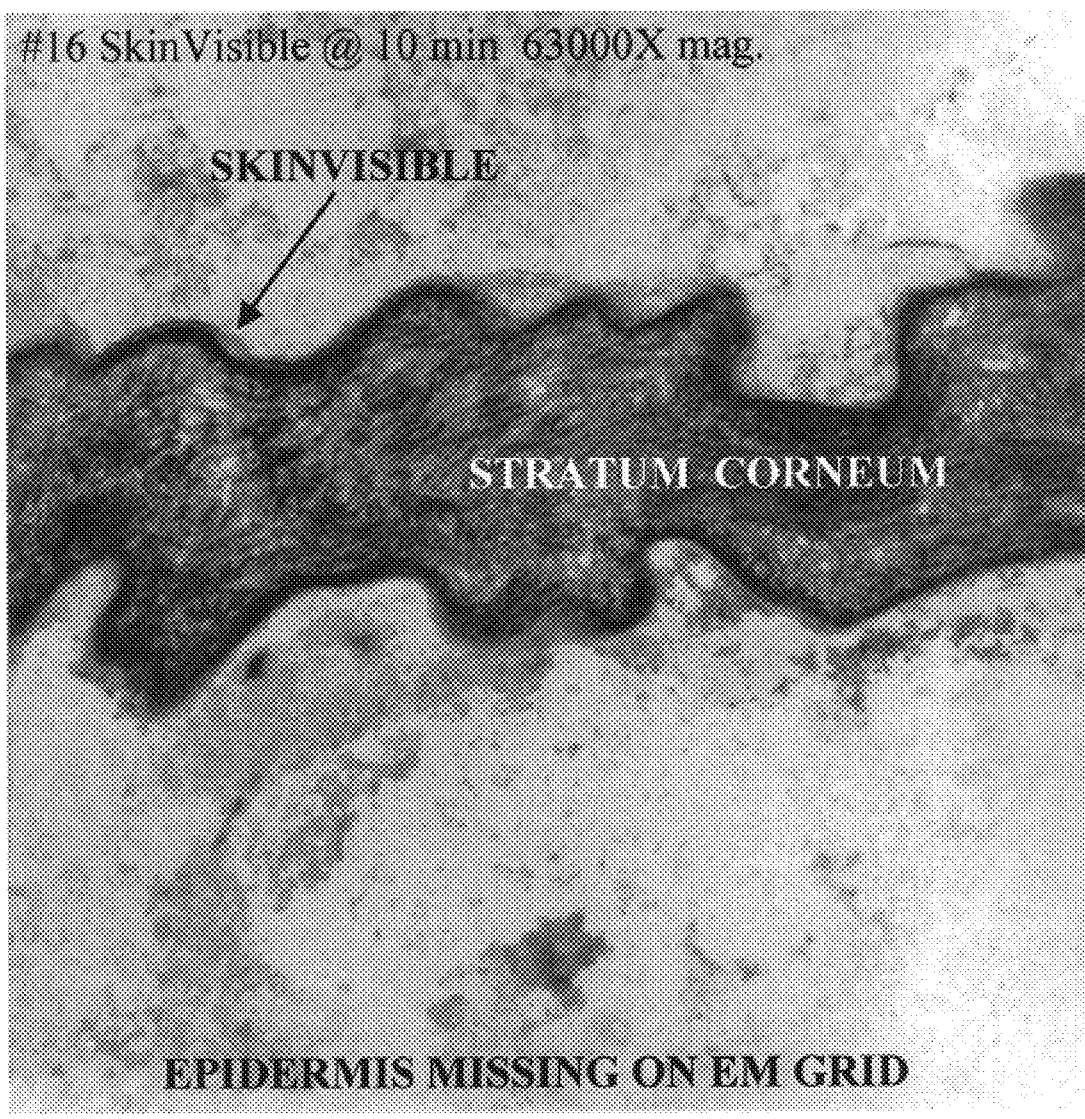
Figure 3:
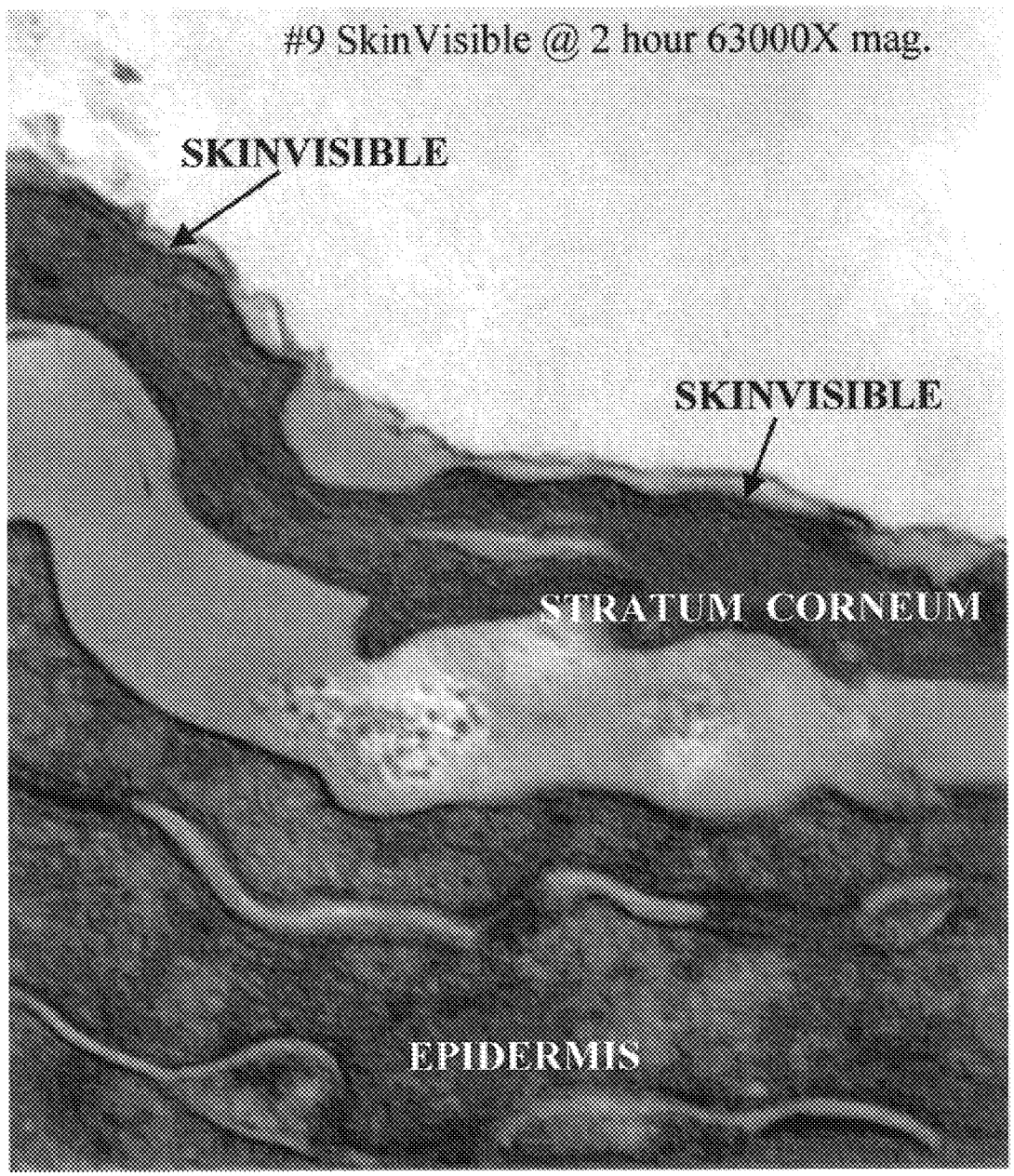
Figure 4:
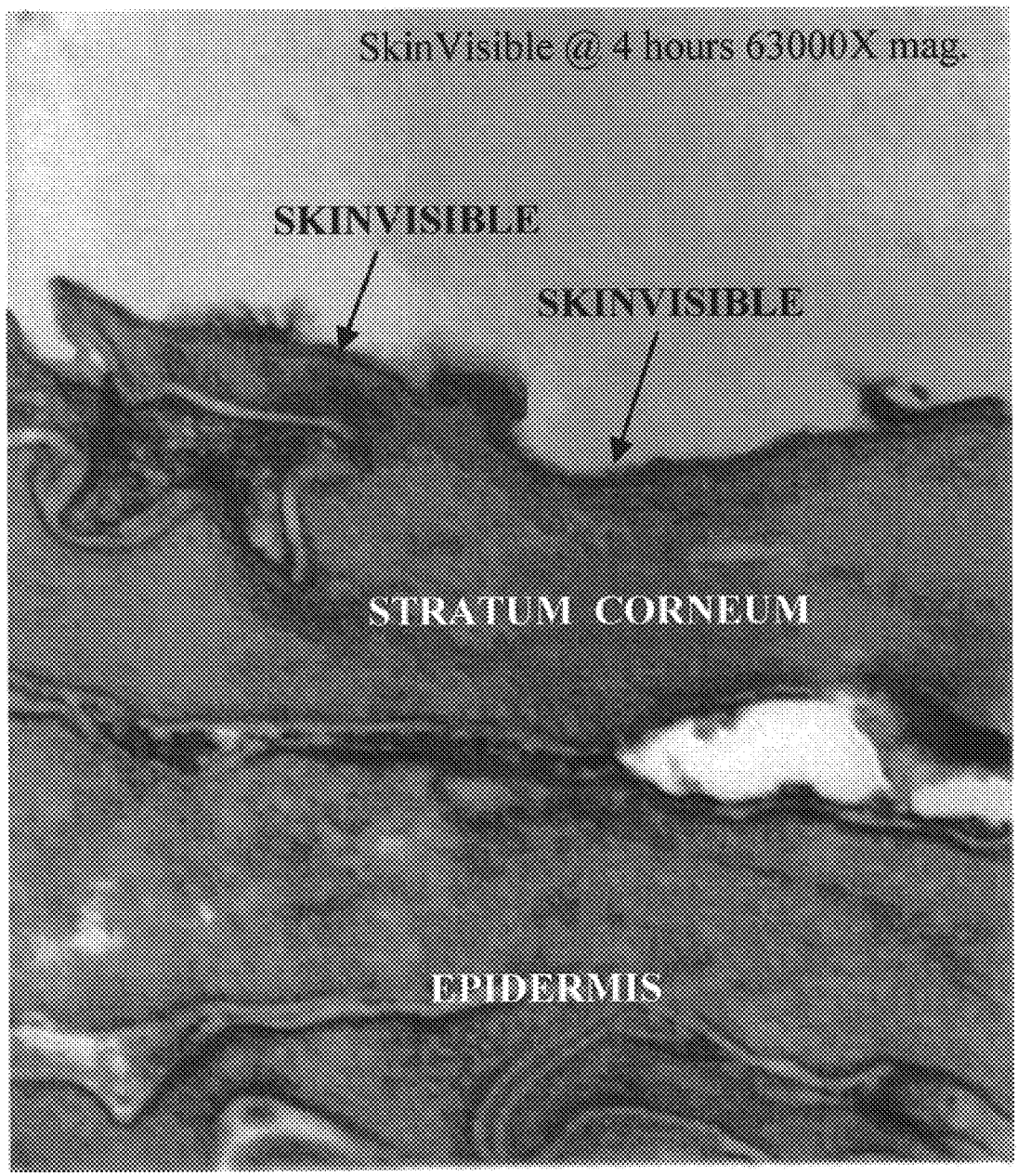
Figure 5:
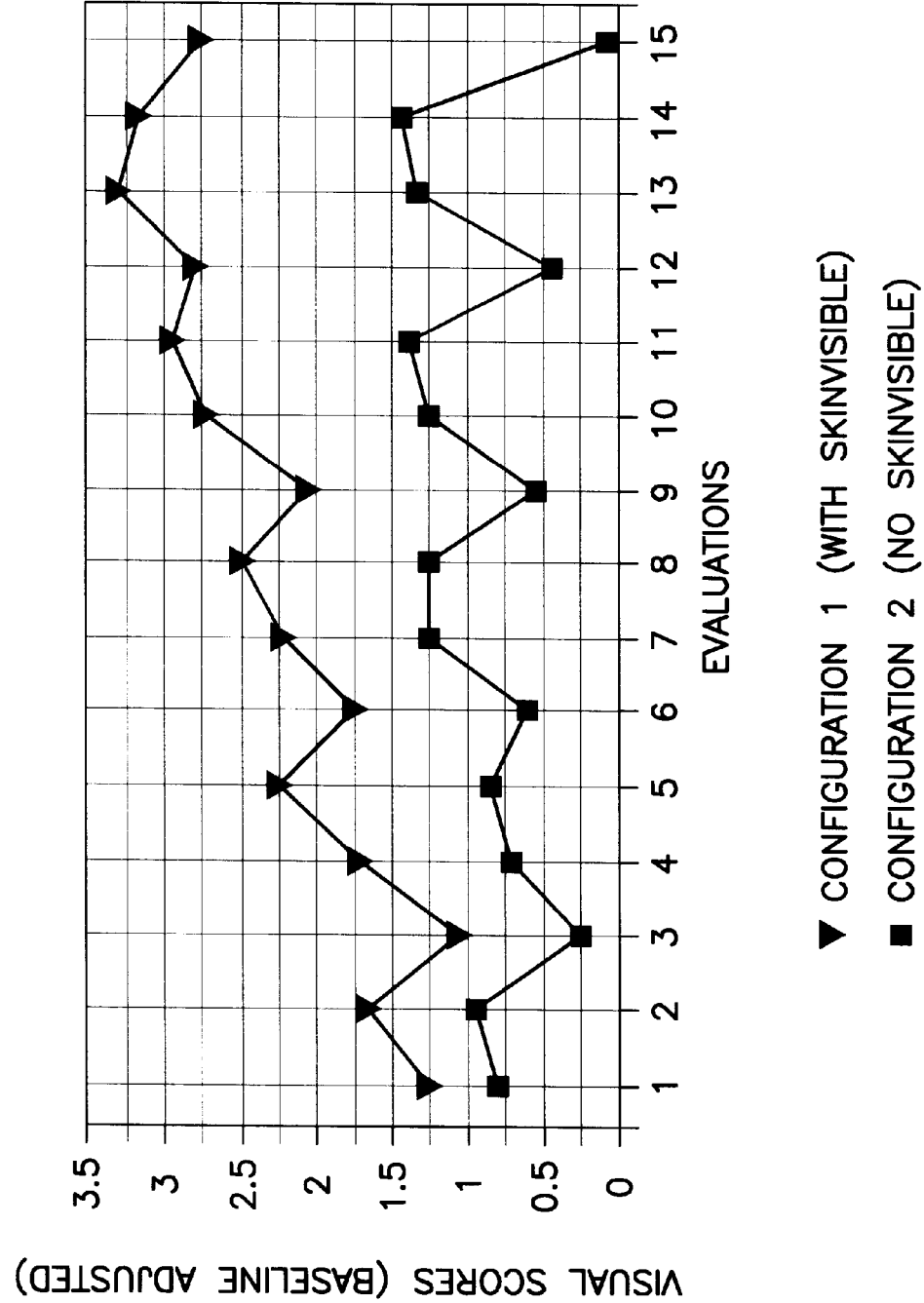
FIG. 5 is a plot showing the visual effects of the dermal barrier compositions of the present invention when used against occupational hand dermatitis.
Figure 6:
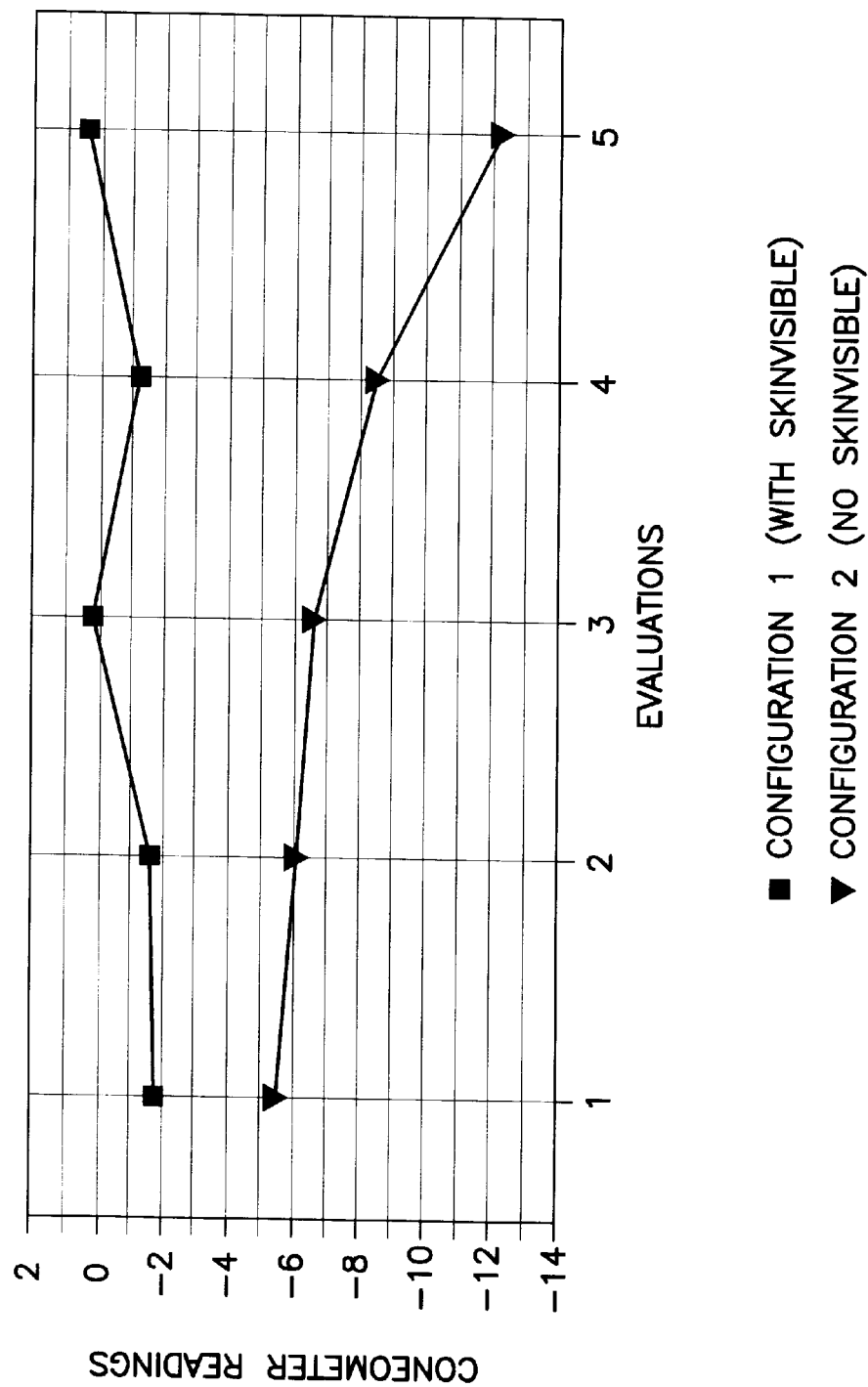
FIG. 6 is a plot showing skin moisture loss, comparing the use of the dermal barrier compositions of the present invention against a control.

The electron microscope photos of FIGS. 2–4 demonstrate that the film not only remained firmly bonded to the stratum corneum, as the film depleted somewhat with time, but that it continued to present a physical barrier even though only in the range of 5–20 nanometers thick. Since the stratum corneum is subject to natural turnover through shedding, the self integrity and plian (i.e. non-brittle) nature of the film is well established.

The other half of the biopsy specimens were analyzed by atomic force microscopy, which in effect provides a high resolution relief map of the surface of the film and the underlying stratum corneum. These studies confirmed the electron microscopy views as to the continuity of the film distribution and also as to the film thickness. The atomic force microscopy also, however, reveals minute somewhat arbitrarily shaped pores, which may be termed "fenestrations", forming with time in the layer. Although irregular in outline, at 2 hours after application they have widths of 100 to 1000 nanometers (0.1 to 1.0 microns), but the cohesiveness and unfractured character of the film remains. In consequence, surface excretions of water and body oils are able to egress, so that the user retains a natural comfortable feeling, but the ingress of harsh or toxic matter, of high molecular weight, is blocked. Thus the physiological properties of the polymeric layer are in a sense asymmetric, in that the user experiences no discomfort such as overheating or moisture accumulation at the hands but is not subject to skin irritation or trauma from harsh or toxic chemicals that may be encountered in health care or food handling situations.

Reapplication, after normal activity, is usually indicated after about four hours after first application. Whether applied manually as an emulsified hand lotion or distributed by spraying or as a pressurized aerosol, the film readily and quickly covers targeted surfaces, typically on the hands. While initially in the form of a low viscosity emulsion that is easily spread, it quickly becomes slightly tacky under the activating influence of bodily fluids on the skin side and air on the exposed side, and then within a short further interval of the order of seconds becomes smooth to the touch and fully pliant and flexible, i.e. nonresistant, to movement of the hands, but non-abraded by objects and matter that is handled.

Example 3

This example deals with dermatological safety. The biocidal dermal barrier composition of Example 1, containing 1% Triclosan®, was tested for possible skin irritation. For a period of 21 days, subjects were daily subjected to fresh patch applications of the biocidal dermal barrier composition and then examined by a dermatologist for evidence of irritation. After completion of the 21 day trial, the subjects were rested for 2 weeks. Then, the subjects were retested to see if any of them had developed a delayed allergy to the test composition. This was done by reapplying a patch containing the biocidal dermal barrier composition. All subjects tolerated the biocidal dermal barrier composition without any visible reaction.

Example 4

This example was conducted to determine the antimicrobial efficacy of the biocidal dermal barrier composition of Example 1. Because of the virulent pathogenicity of some of the organisms in question, the testing was separated into two sections. For those organisms of lesser virulence, human subjects were used for testing the lotion on human skin. For those pathogens deemed too virulent for human contact, fresh pigskin was used instead.

In these studies, the antimicrobial efficacy of the biocidal dermal barrier composition was examined using the Agar Patch Technique. In this study protocol, agar button patches (approximately 2.5 cm in diameter) were inoculated with a known count of specific challenge microorganisms. The patches were then applied to the treated skin for an allocated amount of time and then allowed to further incubate for up to 48 hours. The agar patches were subsequently examined for bacterial growth and if any survival of microorganisms were noted, the colonies were counted and noted as $Log_{10}$ reductions or increases from the baseline state prior to application to the treated skin. All studies were carried out with cohort controls to ensure accuracy.

In the design of the agar patch studies, the challenge organisms chosen for the test protocols were carefully selected as those organisms of most interest to the food supply system and health care personnel use as defined by the HealthCare Cotinuum Model (HCCM) proposed in 1995 by the CTFA and SDA as a comprehensive model to address public and professional use of topical antimicrobial products in these respective workplaces.

Additional attention was taken in the design of the study to validate the parameter of substantivity (the ability of the biocidal dermal barrier to demonstrate bioactivity of its antimicrobial effects over a prolonged interval when applied to skin) for a period of four hours.

Although the standard contact time of inoculated agar patches to treated skin in this study protocol is thirty minutes, the protocol was modified to one minute and five minutes to reflect more accurately the working environments of food handling and health care.

In all agar patch studies, agar patches were applied to the treated skin at 10 minutes, 2 hours and 4 hours following application of the biocidal dermal barrier composition.

The following organisms were approved by Institutional Review Board (IRB) application for human trial studies. The test protocols utilizing human subjects were included to substantiate the equal effectiveness and bioactivity of the biocidal dermal barrier composition when applied to human skin.

Staphylococcus aureus (ATCC #6538)
Staphylococcus epidermidis (ATCC #12228)
Escherichia coli (ATCC #1 1229)
Klebsiella pneumoniae (ATCC #10031)

The following tables summarize the results following contact times at 10 minutes, two hours and four hours post application on treated skin:

Reduction Summary of Klebsiella pneumonia (ATCC #10031)

| Sample | Sample Size | Baseline $Log_{10}$ | Post Product $Log_{10}$ | $Log_{10}$ Reduction | Percent Reduction |
|---|---|---|---|---|---|
| Immediate | 10 | 2.41 | 0.00 | 2.41 | 99.99% |
| 2 Hour | 10 | 2.28 | 0.45 | 1.83 | 98.52% |
| 4 hour | 10 | 2.35 | 1.45 | 0.90 | 87.41% |

Reduction Summary of Staphylococcus aureus (ATCC #6538)

| Sample | Sample Size | Baseline $Log_{10}$ | Post Product $Log_{10}$ | $Log_{10}$ Reduction | Percent Reduction |
|---|---|---|---|---|---|
| Immediate | 10 | 2.71 | 0.03 | 2.68 | 99.79% |
| 2 Hour | 10 | 2.63 | 0.39 | 2.24 | 99.42% |
| 4 hour | 10 | 2.62 | 1.01 | 1.61 | 97.55 |

Reduction Summary of Staphylococcus epidermidis (ATCC #12228)

| Sample | Sample Size | Baseline $Log_{10}$ | Post Product $Log_{10}$ | $Log_{10}$ Reduction* | Percent Reduction* |
|---|---|---|---|---|---|
| Immediate | 10 | 2.46 | 0.00 | 2.46 | 99.65% |
| 2 Hour | 10 | 2.50 | 0.36 | 2.14 | 99.28% |
| 4 hour | 10 | 2.19 | 1.36 | 0.83 | 85.21% |

Reduction Summary of Escherichia coli (ATCC #11229)

| Sample | Sample Size | Baseline $Log_{10}$ | Post Product $Log_{10}$ | $Log_{10}$ Reduction | Percent Reduction |
|---|---|---|---|---|---|
| Immediate | 10 | 2.41 | 0.14 | 2.27 | 99.46% |
| 2 Hour | 10 | 2.34 | 1.81 | 0.53 | 70.49% |
| 4 hour | 10 | 2.39 | 1.97 | 0.42 | 61.98% |

The remainder of the test organisms were carried out using a pigskin substrate model. In this study, inoculated agar patch plates with specific test challenge microorganism species were applied to the fresh samples of treated pigskin and allowed to remain in contact for one minute and five minutes. The $Log_{10}$ reduction of each microorganism from the control plates (inoculated agar patch plates exposed to untreated pigskin) was calculated.

The following is a lift of these organisms and the results of kill for one minute contact times:

| Microorganism Species | ATCC # | Incubation Time (Hours) | Media | Reduction at 1 Min. |
|---|---|---|---|---|
| Enterococcus faecalis MDR/VRE | 51299 | 16–48 | TSB/TSA | 100% |
| Listeria monocytogenes | 7644 | 16–48 | TSB/TSA | 100% |

-continued

| Microorganism Species | ATCC # | Incubation Time (Hours) | Media | Reduction at 1 Min. |
|---|---|---|---|---|
| Salmonella typhi | 6539 | 16–48 | TSB/TSA | 100% |
| Staphylococcus aureus MRSA | 33592 | 16–48 | TSB/TSA | 100% |
| Streptococcus pyogenes | 19615 | 16–48 | BHIB/BHIA | 100% |
| Clostridium perfringens | 13124 | 16–48 | RCM/RCA | 100% |
| Neisseria gonorrheae | 49926 | 16–48 | CHOC-XV | 100% |
| Shigella dysenteriae | Clinical Isolate | 16–48 | TSB/TSA | 100% |
| Vibrio vulnificus | 27562 | 16–48 | MAR | 100% |
| Bacillus cereus** | 14579 | 16–48 | TSB/TSA | 100% |
| Candidas albicans** | 10231 | 16–48 | TSB/SDA | minimal |
| Pseudomonas aeruginosa | 9027 | 16–48 | TSB/TSA | minimal |
| Burkholderia cepacia | 25416 | 16–48 | TSB/TSA | no kill |
| Serratia marcescens | 14756 | 16–48 | TSB/TSA | no kill |

**Bacillus cereus and Candida albicans had contact times of 5 and 30 minutes and 15 and 30 minutes respectively.

Wherein:
TSB is Tryptic Soy Broth
TSA is Tryptic Soy Agar
BHIB is Brain-Heart Infusion Broth
BHIA is Brain-Heart Infusion Agar
RCM is Reinforced Clostridium Medium
RCA is Reinforced Clostridium Agar
CHOC-XV is Chocolate Agar with Bacto Supplement B
MAR is Marine Agar
SDA is Sabouraud Agar In all cases, small buttons of agar inoculated with the organisms in question were placed in contact with the treated surface and then incubated to determine if any organisms had survived contact with the treated surface. Whereas the study profile for this test was designed by the FDA (Federal Food and Drug Administration) for a 30 minute contact period, the biocidal dermal barrier composition was able to achieve 100% kill for most of the organisms within one minute. Note that the biocidal dermal barrier composition proved effective even against methicillin resistant *Staphylococcus aureus* (MRSA) and vancomycin resistant *Enterococcus faecalis* (VRE), which are widely regarded in the heath care industry as superbugs.

Example 5

Using the previously described test protocol, the biocidal dermal barrier composition of Example 1 was tested against food borne pathogens. As seen in the following data, certain foods are categorically associated with particular pathogens. The biocidal dermal barrier composition, containing 1% Triclosan®, proved extremely effective against all tested pathogens.

The results are seen in the following table:

| Food Category | Organism | Source | Exposure time | Contact time | Percent of kill |
|---|---|---|---|---|---|
| poultry | Salmonella typhi | ATCC 6539 | 10 minutes | 1 min/5 min | 100% |
| | | | 2 hours | 1 min/5 min | 100% |
| | | | 4 hours | 1 min/5 min | 100% |
| lettuce | Shigella dysenteriae | clinical isolate | 10 minutes | 1 min/5 min | 100% |
| | | | 2 hours | 1 min/5 min | 100% |
| | | | 4 hours | 1 min/5 min | 100% |
| pork and chicken | Clostridium perfringens | ATCC 13124 | 10 minutes | 1 min/5 min | 100% |
| | | | 2 hours | 1 min/5 min | 100% |
| | | | 4 hours | 1 min/5 min | 100% |
| beef | Escherichia coli | ATCC 51657 | 10 minutes | 1 min/5 min | 100% |
| | | | 2 hours | 1 min/5 min | 100% |
| | | | 4 hours | 1 min/5 min | 100% |
| seafood | Vibrio vulnificus | ATCC 27562 | 10 minutes | 1 min/5 min | 100% |
| | | | 2 hours | 1 min/5 min | 100% |
| | | | 4 hours | 1 min/5 min | 100% |
| dairy | Listeria monocytogenes | ATCC 7644 | 10 minutes | 1 min/5 min | 100% |
| | | | 2 hours | 1 min/5 min | 100% |
| | | | 4 hours | 1 min/5 min | 100% |
| rice | Bacillus cereus | ATCC 14579 | 10 minutes | 1 min/5 min | 100% |
| | | | 2 hours | 1 min/5 min | 100% |
| | | | 4 hours | 1 min/5 min | 100% |

Example 6

The biocidal dermal barrier composition described in Example 1 was tested against a number of toxic chemicals to ascertain its barrier characteristics. After 3 hours, the dermal barrier composition was 99% effective against permeation of the following chemicals. After 6 hours, the barrier composition was at least 97% effective.

One drop (about 0.03 g) of the biocidal dermal barrier composition was carefully spread out on one side of a 7.5 $cm^2$ fritted glass filter using a rubber "policeman". The actual amount was determined by weighing the entire fritted glass before and after application. Alternatively, the amount could have been determined by weighing the loaded policeman before and after application to the surface. Then, one side of the fritted filter was filled with water (chamber B) and the other side was filled with the challenge liquid (chamber A).

After 3 and 6 hours, respectively, a 5–20 ml aliquot of the water was withdrawn from the water side and the concentration of the challenge liquid permeated to the water side was determined by a specific protocol such as gas chromatography, thin layer chromatography, titration, colorimetry, gravimetry, etc. When the 3 hour sample was taken, an equal aliquot of the challenge liquid is also taken to keep the hydrostatic pressure equal for the next three-hour permeation period. The results are summarized in the table below:

| Chamber A Challenge Liquid | Permeation Results* | | | |
|---|---|---|---|---|
| | 3 Hour Chamber B Concentration (weight basis) | 6 Hour Chamber B Concentration (weight basis) | Weight Percent Retained (3 hours) | Weight Percent Retained (6 hours) |
| 16% acetone | 0.18% | 0.47% | 99.9 | 97.1 |
| 10% formaldehyde | 0.04% | 0.07% | 99.6 | 99.3 |
| 5% ammonia | 0.02% | 0.04% | 99.6 | 99.2 |
| 5% NaClO$_2$ | 0.09% | 0.12% | 98.2 | 97.6 |
| 3% H$_2$O$_2$ | 0.036% | 0.060% | 98.8 | 98.0 |
| 10% concentrated HCl | 0.005% | 0.009% | 99.9 | 99.8 |
| 10% NaOH | 0.04% | 0.07% | 99.6 | 99.3 |
| 1% Baygon | 0.005% | 0.007% | 99.5 | 99.3 |
| 1% Malathion | <0.01% | <0.01% | >99 | >99 |
| 1% Dursban | <0.01% | <0.01% | >99 | >99 |
| 1% Atrazine | <0.01% | <0.01% | >99 | >99 |
| 100% perchloroethylene | 0.670% | 0.673% | 99.33 | 99.33 |
| 100% methylene chloride | 28.6 vol % | 31.8 vol % | 28.6 | 31.8** |
| 100% gasoline | 3.3 ppm | 3.4 ppm | 96.7 | 96.6 |
| 100% diesel fuel | 2.1 ppm | 2.1 ppm | 99.99 | 99.99 |
| 100% paint thinner | <1 ppm | 27 ppm | 99.99 | 99.99 |
| 100% paint stripper | 7.7 ppm | 37.0 ppm | 99.99 | 99.99 |
| 6% latex with protein | <0.005 (4 hrs) | | >99.92 | |
| 1% D&C Red 33 | 9.8 ppm | 20.9 ppm | 99.90 | 99.71 |
| 1% D&C Green 28 | <10 ppm | <10 ppm | >99.90 | >99.90 |
| 1% D&C Green 6 | 0.037 ppm | 2.53 ppm | 99.99 | 99.97 |
| 1% D&C Yellow 5 | 18.4 ppm | 45.9 ppm | 99.82 | 99.64 |
| 1% D&C Red 4 | 1.86 ppm | 14.8 ppm | 99.88 | 99.85 |
| 1% D&C Red 40 | 0.019 ppm | 8.50 ppm | 99.99 | 99.91 |
| 1% D&C Blue 1 | 2.98 ppm | 10.48 ppm | 99.97 | 99.90 |
| 1% D&C Red 3 | 14.8 ppm | 22.68 ppm | 99.85 | 99.77 |
| 100% wax stripper | 84.7 ppm | 226 ppm | 99.99 | 99.98 |

*A negative control for acetone was run and the permeation rate for 16% acetone was 0.32% after 3 hours. Several challenge liquids, especially methylene chloride, show more permeation.
**This small molecule and powerful solvent passes through many materials.

Example 7

The AIDS virus (HIV) and Influenza A virus were chosen to represent the envelope virus group. The results of the studies were reasonably predictable. In both the pigskin and human trials, the viruses represented by the envelope group HIV and Influenza A were predictably killed to levels representing minimal infective rates whereas the NON-envelope group (including Hepatitus A, Rotavirus and Rhinovirus) showed only a modest reduction when subjected to contact with the biocidal dermal barrier composition.

The HTLV-III$_B$ strain of Human Immunodeficiency Virus Type 1 (HIV-1) used for this study was obtained from Vanderbilt University. Stock virus was prepared by cooling the supernatant culture fluid from infected culture cells as determined by an indirect immunofluorescence assay specific for the HIV-1 antigen. The cells were disrupted and cell debris removed by centrifugation at approximately 2800 RPM for 15 minutes at approximately 20° C. The supernatant was removed, aliquoted, and the high titer stock virus was stored at about 60° C. until the day of use. On the day of use an aliquot of stock virus (ViroMed Lot VML-IIIB-48) was removed, thawed and refrigerated until use in the assay. The stock virus cultures contained 5% fetal bovine serum as the organic soil load. The stock virus tested demonstrated cytopathic effects (CPE) typical of HIV on MT-2 cells.

MT-2 cells (human CD4+ lymphocytes) were originally obtained from the National Cancer Institute, Frederick, Md. Cultures were grown and propagated in-house and used in suspension in disposable tissue culture labware. On the day of testing, cells were observed as having proper cell integrity and therefore, were acceptable for use in this study.

The test media used in this study was RPMI 1640 supplemented with 15% (v/v) fetal bovine serum (fbs) heat-inactivated at approximately 56° C. for 30 minutes. The media was also supplemented with 2.0 mM L-glutamine and 50 mg/ml gentamicin.

The following is a list of the test and control groups, usual dilutions and number of cultures assayed.

| Parameter | Summary | Dilutions to be Assayed | Cultures |
|---|---|---|---|
| Cell Control | Medium Alone | NA | 4/group |
| Virus Control (untreated) | Medium + Virus* | $10^{-2}$ to $10^{-7}$ | 4/diln |
| Virucidal Test (treated) | Antimicrobial Solution + Virus* | $10^{-2}$ to $10^{-7}$ | 4/diln |
| Cytotoxicity Control | Antimicrobial Solution + Medium | $10^{-2}$ to $10^{-7}$ | 4/diln |
| Neutralization Control | Neutralized Antimicrobial Solution + Virus | $10^{-2}$ to $10^{-7}$ | 4/diln |

*Three separate drying periods were performed using two replicates each.

A square of pig skin approximately five centimeters by five centimeters in dimension was utilized for each test and control parameter. The skin was sterilized by immersion into an alcohol solution followed by rinsing with sterile deionized water.

A 0.5 ml aliquot of the biocidal dermal barrier composition was applied to the surface of two separate pieces of pig skin, contained in a sterile vesicle, for each drying period. Three separate drying periods were performed, ten minutes, two hours, and four hours. Following the application of the biocidal to the skin, it was allowed to dry for the requested periods at 37° C. in a humidified chamber. The test virus suspension was thoroughly mixed. A 0.2 ml aliquot of the virus suspension was inoculated onto the surface of each skin assuring that the virus suspension covered the entire square of skin without allowing any to leave the skin. The virus suspension was spread across each skin utilizing a sterile glass rod. The virus remained in contact with the treated skin for the one-minute exposure period at room temperature (22° C.). Following the exposure period, the skin/virus combination was carefully removed from the vesicle and placed into a sterile vesicle containing a 15.0 ml aliquot of test media. Immediately, the solution was placed into a sonnicated water bath for 30 seconds, followed immediately by vigorous mixing using a vortex mixer. Serial 10-fold dilutions were then immediately performed (0.1 ml+0.9 ml test media) and the dilutions assayed for the presence of virus.

A 0.5 ml aliquot of test media (the same volume as the biocidal solution) alone was inoculated onto two separate squares of pigskin for each drying period. One square was held for each of the 10 minute, two hour, and four hour drying periods at approximately 37° C. in a humidified chamber and treated as previously described. The virus control was run in parallel to the test virus. Following each of the drying periods, a 0.2 ml aliquot of the test virus was inoculated onto the surface of each skin, spread across the skin utilizing a sterile glass rod and held for the requested one-minute exposure period at room temperature (22° C.). Following the exposure period, the skin was placed into a vesicle containing 15.0 ml of test media and processed as previously described. The corresponding average virus control titer was used as a baseline to compare the log reduction of each test parameter following exposure to the biocidal.

A square of pig skin was inoculated with 0.5 ml of the biocidal solution as previously described. Following the drying period, test media alone was inoculated onto the surface of the skin in lieu of virus. The media remained in contact with the treated skin for the one-minute exposure period at room temperature (22° C.). Following the exposure period, the skin/media combination was carefully removed from the vesicle and placed into a sterile vesicle containing a 15.0 ml aliquot of test media. Immediately, the solution was placed into a sonnicated water bath for 30 seconds, followed immediately by vigorous mixing using a vortex mixer. Serial 10-fold dilutions were then immediately performed (0.2 ml+1.8 ml test media) and the dilutions assayed for cytotoxic effects. Cytotoxicity was graded on the basis of cell viability as determined microscopically. Cellular alterations due to toxicity were graded and reported toxic (T) if greater than or equal to 50% of the monolayer was affected.

Serial dilutions of the diluted neutralized biocidal solution (cytotoxicity control dilutions) were mixed with low titer stock virus. The resulting mixtures of dilutions were assayed for infectivity and or cytotoxicity in order to determine the dilution(s) of antimicrobial solution at which virucidal activity, if any, was retained. Dilutions that show virucidal activity were not considered in determining reduction in infectivity by biocidal solution.

The MT-2 cell line, which exhibits CPE in the presence of HIV-1, was used as the indicator cell line in the infectivity assays. Cells in multiwell culture dishes were inoculated in quadruplicate with 0.2 ml of the dilutions prepared from test and control groups. Uninfected indicator cell cultures (cell controls) were inoculated with test media alone. Cultures were incubated at 38° C. in a humidified atmosphere of 6.0% $CO_2$ in sterile disposable cell culture labware. The cultures were scored periodically for eight days for the absence of presence of CPE, cytotoxicity, and for viability.

Viral and cytotoxicity titers are expressed as $-\log_{10}$ of the 50 percent titration endpoint for infectivity ($TCID_{50}$) or cytotoxicity ($TCD_{50}$), respectively, as calculated by the method of Spearman Karber. The method of Karber is used to calculate 50 percent endpoints:

$$-1 - \left[ \frac{\text{Sum of \% mortality at each dilution}}{100} - .5 * (\text{logarithm of dilution}) \right]$$

$$\% \text{ Reduction} = 1 - \left[ \frac{TCID_{50} \text{ test}}{TCID_{50} \text{ virus control}} \right] * 100$$

10 Minute Drying Period

The titer of the virus control was 6.5 $\log_{10}$ for both replicates tested. Following exposure, test virus infectivity was detected in the virus-test substance mixture at any dilution tested ($\leq 3.5 \log_{10}$) for both replicates tested. Test substance cytotoxicity was observed at 3.5 $\log_{10}$. The neutralization control (non-virucidal level of the test substance) indicates that the test substance was neutralized at $\leq 3.5 \log_{10}$. Under these test conditions, the biocidal dermal barrier composition demonstrated complete inactivation of the HIV-1. Following a one-minute exposure period, the average log reduction in virus titer of the two replicates tested was $\geq 3.0 \log_{10}$. The average percent reduction was $\geq 99.9\%$.

2 Hour Drying Period

The titer of the virus control was 6.0 $\log_{10}$ for both replicates tested. Following exposure, test virus infectivity was detected in the virus-test substance mixture at $\leq 3.5 \log_{10}$ for both replicates tested. Test substance cytotoxicity was observed at 3.5 $\log_{10}$. The neutralization control (non-virucidal level of the test substance) indicates that the test substance was neutralized at $\leq 3.5 \log_{10}$. Under these test conditions, the biocidal dermal barrier composition demonstrated complete inactivation of the HIV-1. Following a one-minute exposure period, the average log reduction in virus titer of the two replicates tested was 2.5 $\log_{10}$. The average percent reduction was $\geq 99.7\%$.

4 Hour Drying Period

The titer of the virus control was 6.0 $\log_{10}$ for both replicates tested. Following exposure, test virus infectivity was detected in the virus-test substance mixture at $\leq 3.5 \log_{10}$ for both replicates tested. Test substance cytotoxicity was observed at 3.5 $\log_{10}$. The neutralization control (non-virucidal level of the test substance) indicates that the test substance was neutralized at $\leq 3.5 \log_{10}$. Under these test conditions, the biocidal dermal barrier composition demonstrated complete inactivation of the HIV-1. Following a one-minute exposure period, the average log reduction in virus titer of the two replicates tested was 2.5 $\log_{10}$. The average percent reduction was $\geq 99.7\%$.

Example 8

The Hong Kong strain of Influenza virus type $A_2$ (ATCC VR-544) used for this study was obtained from the American Type Culture Collection, Rockville, Md. Stock virus was prepared by collecting the supernatant culture fluid from infected culture cells. The cells were disrupted and cell debris removed by centrifugation at approximately 2200 RPM for five minutes at approximately 4° C. The supernatant was removed, aliquoted, and the high titer stock virus was stored at about 70° C. until the day of use. On the day of use, an aliquot of stock virus (ViroMed Lot VML-F44) was removed, thawed and refrigerated until use in the assay. The stock virus cultures contained 1% fetal bovine serum as the organic soil load. The stock virus tested demonstrated cytopathic effects (CPE) typical of Influenza virus type $A_2$ on Rhesus monkey kidney cells.

Rhesus monkey kidney (RMK) cells were obtained from ViroMed Laboratories, Inc. Cell Culture Division. Cultures were grown and propagated in-house and used as monolayers in disposable tissue culture labware. On the day of testing, cells were observed as having proper cell integrity and therefore, were acceptable for use in this study.

Test media used in this study was Eagles minimal essential medium (E-MEM) supplemented with 1% heat-inactivated fetal bovine serum (fbs), 10 mg/ml gentamicin, 100 units/ml penicillin, and 2.5 mg/ml Fungizone.

The following is a list of the test and control groups, usual dilutions and number of cultures assayed.

| Parameter | Summary | Dilutions to be Assayed | Cultures |
|---|---|---|---|
| Cell Control | Medium Alone | | 4/group |
| Virus Control (untreated) | Medium + Virus* | $10^{-2}$ to $10^{-8}$ | 4/diln |
| Virucidal Test (treated) | Antimicrobial Solution + Virus* | $10^{-2}$ to $10^{-8}$ | 4/diln |
| Cytotoxicity Control | Antimicrobial Solution + Medium | $10^{-2}$ to $10^{-8}$ | 4/diln |
| Neutralization Control | Neutralized Antimicrobial Solution + Virus | $10^{-2}$ to $10^{-8}$ | 4/diln |

*Three separate drying periods were performed using one replicate each.

Test procedures not described herein were identical to those used in Example 7.

The RMK cell line, which exhibits CPE in the presence of Influenza virus type $A_2$ was used as the indicator cell line in the infectivity assays. Cells in multiwell culture dishes were inoculated in quadruplicate with 0.1 ml of the dilutions prepared from test and control groups. Uninfected indicator cell cultures (cell controls) were inoculated with test media alone. Cultures were incubated at 37° C. in a humidified atmosphere of 5.6–6.5% $CO_2$ in sterile disposable cell culture labware. The cultures were scored periodically for seven days for the absence of presence of CPE, cytotoxicity, and for viability.

Viral and cytotoxicity titers are expressed as $-\log_{10}$ of the 50 percent titration endpoint for infectivity ($TCID_{50}$) or cytotoxicity ($TCD_{50}$), respectively, as previously described.

The titer of the virus control was 6.75 log,, for the 10-minute drying period, 8.0 $\log_{10}$ for the 2 hour drying period and 6.5 $\log_{10}$ for the 4-hour drying period. Following exposure, test virus infectivity was not detected in the virus-test substance mixture at any drying period (2.5 $\log_{10}$ for the 10-minute and 4-hour drying periods and 3.5 $\log_{10}$ for the 2-hour drying period). Test substance cytotoxicity was observed at 2.5 $\log_{10}$. The neutralization control (non-virucidal level of the test substance) indicates that the test substance was neutralized at 2.5 $\log_{10}$. Taking the cytotoxicity and neutralization control results into consideration, the reduction in virus titer following a one minute exposure period was 4.25 $\log_{10}$ for the 10 minute drying period, 4.5 $\log_{10}$ for the 2 hour drying period, and 4.0 $\log_{10}$ for the 4 hour drying period. The percent reductions were 99.994%, 99.997%, and 99.99% respectively. Under these test conditions, the biocidal dermal barrier composition demonstrated complete inactivation of the Influenza virus type $A_2$.

Example 9

A study was undertaken to determine if the dermal barrier compositions of the present invention would have an impact on occupational hand dermatitis. Twenty test subjects underwent repeated handwashing with a commercially available antimicrobial soap. Ten subjects used the dermal barrier composition of the present invention while ten subjects functioned as a control group by using no barrier. The test group underwent three dermal barrier composition applications per day and ten washes with Hibiclens® (a well known antimicrobial hand soap used in the health care industry) per day. The control group underwent ten handwashes per day with Hibiclens®. Both groups continued for a total of five days.

For each handwashing, subjects were instructed to wash for at least 30 seconds and then to rinse for at least 30 seconds. Subjects were instructed to wait at least 30 minutes between wash cycles. At the start of each day, subjects reported in for a visual inspection of their hands. At that time, members of the test group received and applied 2 milliliters of the dermal barrier composition of the invention.

FIG. 5 demonstrates certain advantages of using the dermal barrier composition. As the number of evaluations increases (indicating an increase in the total number of handwashing episodes), the control group subjects demonstrated a substantial increase in observable signs of OHD. In contrast, the test group remained remarkably constant.

FIG. 6 shows Corneometer® scores, which measures the skin's moisture content. The plot indicates that the skin moisture contents steadily fell for the control group. In contrast, the test group remained fairly constant. In fact, the test group exhibited a slight increase in skin moisture content over the 5 day test period.

The foregoing description, examples and data are illustrative of the invention described herein, and they should not be used to unduly limit the scope of the invention or the claims. Since many embodiments and variations can be made while remaining within the spirit and scope of the invention, the invention resides wholly in the claims hereinafter appended.

I claim:

1. A dermal composition for topical application comprising:

an emulsion comprising a mixture of polymers, (i), (ii) and (iii), each polymer having a size that allows for mixing and barrier properties, wherein the mixture of polymers comprises:

(i) poly(methyl vinyl ether/maleic acid) provided in an amount of up to 69.6 wt.%, based on the weight of the mixture of polymers;

(ii) at least 3 wt.%, based on the weight of the mixture of polymers, of poly(vinyl pyrrolidone/1-eiocosene);

(iii) poly(vinyl pyrrolidone/1-hexadecene) provided in an amount of up to 51.5 wt. %, based on the weight of the mixture of polymers; and water.

2. The dermal composition according to claim 1, wherein the amount of the poly(vinyl pyrrolidone/1 -eicosene) is from 3 wt.% to 7.5 wt. %, based on the weight of the mixture of polymers.

3. The dermal composition according to claim 1, wherein the amount of the poly(vinyl pyrrolidone/1-hexadecene) is from 45.5 wt.%, to 51.5 wt.%, based on the weight of the mixture of polymers.

4. The dermal composition according to claim 1, wherein the amount of the poly(vinyl pyrrolidone/1-hexadecene) is from 27.7 wt.%, to 32.9 wt.%, based on the weight of the mixture of polymers.

5. The dermal composition according to claim 1, wherein the dermal composition, when applied to dry fritted glass in a thickness of about 0.5 to about 0.85 millimeters and allowed to bond to the glass for a period of 30 seconds, provides a film which remains at least about 80% adhered to the fritted glass after treatment with 5% ammonium hydroxide for a period of three hours.

6. The dermal composition according to claim 1, wherein the poly(methyl vinyl ether/maleic acid) has a number average molecular weight of less than about 95,000.

7. The dermal composition according to claim 1, wherein the poly(vinyl pyrrolidone/1-eicosene) has a number average molecular weight of at least 5,000.

8. The dermal composition according to claim 1, wherein the poly(vinyl pyrrolidone/1-hexadecene) has a number average molecular weight of at least 5,000.

9. The dermal composition according to claim 1, further comprising a biocide.

10. The dermal composition according to claim 9, wherein the biocide comprises at least one of an ammonium compound and a peroxygen compound.

11. The dermal composition according to claim 9, wherein the biocide comprises peroxy acid.

12. The dermal composition according to claim 9, wherein the biocide comprises chlorinated diphenyl ether.

13. The dermal composition according to claim 1, further comprising a fungicide.

14. The dermal composition according to claim 13, wherein the fungicide comprises at least one of clotrimazole nitrate, miconazole nitrate, sulconazole, naftifine, morpholine, allylamine, and triazole.

15. The dermal composition according to claim 1, further comprising an insecticide.

16. The dermal composition according to claim 15, wherein the insecticide comprises at least one of citronella and N,N'-diethyl-3-methylbenzamide.

17. The dermal composition according to claim 1, further comprising a sunscreen.

18. The dermal composition according to claim 17, wherein the sunscreen comprises at least one of aminobenzoic acid, cinoxate, diethanolamine methoxycinnamate, digalloyl trioleate, dioxybenzone, ethyl 4[bis(hydroxypropyl)]aminobenzoate, glyceryl aminobenzoate, homosalate, lawsone with dihydroxyacetone, menthyl anthranilate, octocrylene, octyl methoxycinnamate, octyl salicylate, oxybenzone : benzophenone, padimate, phenylbenzimidazole sulfoninc acid, red petrolaum, sulisobenzone, titanium dioxide, trolamine salicylate, and mixtures thereof.

* * * * *